United States Patent [19]

Aldag, Jr.

[11] Patent Number: 4,477,592

[45] Date of Patent: Oct. 16, 1984

[54] CATALYST FOR SKELETAL ISOMERIZATION

[75] Inventor: Arthur W. Aldag, Jr., Bartlesville, Okla.

[73] Assignee: Phillips Petroleum Company, Bartlesville, Okla.

[21] Appl. No.: 573,163

[22] Filed: Jan. 23, 1984

Related U.S. Application Data

[62] Division of Ser. No. 443,720, Nov. 22, 1982, Pat. No. 4,446,013.

[51] Int. Cl.³ .................. B01J 21/04; B01J 21/06; B01J 23/06
[52] U.S. Cl. .................................... 502/342; 502/343
[58] Field of Search .................. 502/242, 342, 343

[56] References Cited

U.S. PATENT DOCUMENTS

| | | | |
|---|---|---|---|
| 2,274,634 | 3/1942 | Heard | 208/135 |
| 4,144,277 | 3/1979 | Walker et al. | 585/433 |
| 4,176,140 | 11/1979 | Bertus et al. | 585/629 |
| 4,218,346 | 8/1980 | Walker et al. | 502/343 |
| 4,327,238 | 4/1982 | Eastman | 585/661 |

Primary Examiner—W. J. Shine
Attorney, Agent, or Firm—French and Doescher

[57] ABSTRACT

The catalytic reforming of a feedstock which contains a derivative of cyclopentane or which contains organic compounds which are convertible to a derivative of cyclopentane is carried out in the presence of a hydrogel of zinc titanate and a suitable acidic material. Also, the attrition resistance of zinc titanate is improved by incorporating the zinc titanate into a hydrogel structure.

10 Claims, No Drawings

CATALYST FOR SKELETAL ISOMERIZATION

This application is a division of application Ser. No. 443,720, filed Nov. 22, 1982, now U.S. Pat. No. 4,446,013.

This invention relates to a process for the skeletal isomerization of derivatives of cyclopentane, and a catalyst therefor. This invention also relates to a method for improving the attrition resistance of a zinc titanate catalyst.

Petroleum processing requires a number of separate process steps to change the petroleum feed stock into desired products. An initial process step which is frequently utilized is reforming.

Reforming is the term which is utilized to refer to a number of process steps which are all designed to increase the octane number of gasoline range materials having a normal boiling range between about 50° C. and about 200° C. (generally referred to as a naphtha feedstock). The most important aspect of reforming is the dehydrogenation of cyclohexane and its derivatives to aromatics. Other aspects of reforming are the cyclization of paraffins to either cyclopentane and its derivatives or cyclohexane and its derivatives. Paraffins cyclized to derivatives of cyclopentane are isomerized to cyclohexane and its derivatives for subsequent aromatization.

Hydrogen must be added to the reforming process to prevent the derivatives of cyclopentane which are present in the naphtha feedstock or which are produced by the cyclization of paraffins from being converted to carbon which will very quickly foul the reforming catalyst. In the presence of hydrogen, derivatives of cyclopentane are isomerized to cyclohexane and its derivatives. Cyclohexane and its derivatives may be dehydrogenated to aromatics and the fouling of the catalyst is substantially prevented.

U.S. Pat. No. 4,263,133 discloses that zinc titanate is effective as a reforming catalyst. However, while zinc titanate is an excellent catalyst for many of the process steps which are included in reforming, the zinc titanate catalyst of U.S. Pat. No. 4,263,133 exhibits little activity with respect to the isomerization of derivatives of cyclopentane to cyclohexane and its derivatives. Since this isomerization step is important in the reforming of feed stocks which contain derivatives of cyclopentane, it is an object of this invention to improve the activity of the zinc titanate catalyst of U.S. Pat. No. 4,263,133 for the skeletal isomerization of derivatives of cyclopentane.

The zinc titanate catalyst of U.S. Pat. No. 4,263,133 is regenerated periodically by contacting the zinc titanate catalyst with free oxygen. This regeneration requirement suggests that when the zinc titanate catalyst is used as a reforming catalyst it could be advantageously used in a moving bed or transfer line reactor. However, while the zinc titanate catalyst of U.S. Pat. No. 4,263,133 can be used in a moving bed or transfer line reactor, it would be desirable to improve the attrition resistance of the zinc titanate catalyst since an attrition resistant catalyst is desirable for use in a moving bed or transfer line reactor. It is thus another object of this invention to provide a method for improving the attrition resistance of the zinc titanate catalyst of U.S. Pat. No. 4,263,133.

In accordance with the present invention, a zinc titanate catalyst is mixed with a hydrosol of a suitable acidic material. A suitable base is then added to the resulting mixture to form a hydrogel. The hydrogel is dried slowly and calcined to form what will be referred to as a zinc titanate hydrogel.

The zinc titanate hydrogel is utilized as a catalyst in a reforming process. The reforming process preferably has alternate reaction periods and regeneration periods. The reforming process is carried out under suitable conditions in the substantial absence of free oxygen. Hydrogen is added to the reforming process. The catalyst regeneration process is carried out in the presence of a free oxygen containing gas to remove carbonaceous material which may have formed on the zinc titanate hydrogel during the reforming process. The use of the zinc titanate hydrogel results in an improved isomerization of derivatives of cyclopentane to cyclohexane and its derivatives over that seen with the zinc titanate catalyst of U.S. Pat. No. 4,263,133 which has the effect of enhancing the octane yield from a naphtha feed stock. Also, the zinc titanate hydrogel exhibits an improved attrition resistance with respect to the zinc titanate catalyst of U.S. Pat. No. 4,263,133 which is advantageous when using a moving bed or transfer line reactor.

Other objects and advantages of the invention will be apparent from the foregoing brief description of the invention and the appended claims, as well as the detailed description of the invention which follows.

Any suitable reformable organic compound can be reformed in accordance with the present invention. Organic compounds which are considered to be advantageously and efficiently reformed in accordance with the process of this invention are the gasoline range materials having a normal boiling range between about 50° C. and about 205° C. The invention is particularly directed to the reforming of gasoline range materials which contain derivatives of cyclopentane at some point in the reforming process.

The feed stock may contain sulfur compounds without impairing the activity of the catalyst. However, sulfur will generally be converted to hydrogen sulfide at reforming conditions. Thus, it is preferable to use desulfurized feed to obviate the need for removal of the hydrogen sulfide downstream from the reformer.

The reforming catalyst employed in the process of the present invention is zinc titanate in a hydrogel of a suitable acidic material. In general, the catalyst composition is prepared by first preparing zinc titanate which is then reduced to a small size. The resulting material is mixed with a hydrosol of a suitable acidic material. A suitable base is then added to the mixture to form a hydrogel. The resulting hydrogel is dried slowly and calcined to form the zinc titanate hydrogel catalyst of the present invention.

The zinc titanate portion of the catalyst composition may be prepared by initimately mixing suitable portions of zinc oxide and titanium dioxide, preferably in a liquid such as water, and calcining the mixture in the presence of free oxygen at a temperature in the range of about 650° C. to about 1050° C., preferably in the range of about 675° C. to about 975° C., to form zinc titanate. A calcining temperature in the range of about 800° C. to about 850° C. is most preferred because the surface area of the zinc titanate is maximized in this temperature range, thus producing a more active zinc titanate. The titanium dioxide used in preparing the zinc titanate preferably has extremely fine particle size to promote intimate mixing of the zinc oxide and titanium dioxide. This produces a rapid reaction of the zinc oxide and titanium dioxide which results in a more active zinc titanate. Preferably the titanium dioxide has an average particle size of less than 100 millimicrons and more preferably less than 30 millimicrons. Flame hydrolyzed titanium dioxide has extremely small particle size and is particularly preferred in preparing the zinc titanate. The atomic ratio of zinc to titanium can be any suitable ratio. The atomic ratio of zinc to titanium will generally lie in the range of about 1:1 to about 3:1 and will preferably lie in the range of about 1.8:1 to about 2.2:1 because the activity of the zinc titanate is greatest for atomic ratios of zinc to titanium in this range. The term "zinc titanate" is used regardless of the atomic ratio of zinc to titanium.

The zinc titanate portion of the catalyst composition may also be prepared by coprecipitation from aqueous solutions of a zinc compound and a titanium compound. The aqueous solutions are mixed together and the hydroxides are precipitated by the addition of ammonium hydroxide. The precipitate is then washed, dried and calcined, as described in the preceding paragraph, to form zinc titanate. This method of preparation is less preferred than the mixing method because the zinc titanate prepared by the coprecipitation method is softer than the zinc titanate prepared by the mixing method.

The resulting zinc titanate is reduced to a suitable size for mixing with a hydrosol of an acidic material by any suitable method such as treatment in an ultrasonic disrupter. The zinc titanate may be reduced to any suitable size with a particle size in the range of about 1 to about 5 microns being preferred.

The resulting zinc titanate having a fine particle size is mixed with a hydrosol of a suitable acidic carrier. Any suitable acidic carrier such as an alumina, a silica-alumina or a zeolite material may be utilized. An alumina is preferred because it forms a well dispersed hydrosol phase. Alumina hydrate is particularly preferred because a hydrosol of alumina hydrate is readily converted to a hydrogel and then to the oxide phase after calcination.

After the zinc titanate has been thoroughly mixed into the hydrosol, a suitable base is added to convert the hydrosol to a hydrogel. Any suitable base such as alkali metal hydroxides, ammonium hydroxide, or urea may be utilized. Ammonium hydroxide is the preferred base because it does not have any metallic component that would remain in the hydrogel.

The resulting hydrogel is dried slowly so that water will not be removed so rapidly that the hydrogel structure will collapse which would result in excessive loss of pore volume and surface area of the finished zinc titanate hydrogel. Any suitable drying time can be utilized which does not result in too rapid removal of water. Preferably, the drying time is in the range of about 8 hours to about 24 hours.

Any suitable temperature can be utilized for the drying of the zinc titanate hydrogel but again the temperature should be such that too rapid a removal of water does not result. The temperature is preferably in the range of about 35° C. to about 150° C. The most preferred drying condition is to start the drying process at about 80° C. and increase the temperature slowly to about 120° C. during the drying time.

After the zinc titanate hydrogel has been dried, the zinc titanate hydrogel is calcined in the presence of free oxygen. Any suitable free oxygen-containing gas may be utilized with air being preferred because of its availability. Also, any suitable time and temperature for the calcining may be utilized with a preferred time being about two hours and a preferred temperature being in the range of about 425° C. to about 650° C. and more preferably in the range of about 480° C. to about 600° C. Although the dried zinc titanate hydrogel can be placed directly into a preheated furnace or kiln for calcining, it is preferable for the catalyst to attain its final temperature during a heating period of about two hours.

The finished catalyst composition can contain any suitable weight percent of zinc titanate. In general, the amount of zinc titanate in the finished catalyst composition will be in the range of from about 10 weight percent to about 50 weight percent based on the total weight of the catalyst composition and will more preferably be in the range of from about 20 weight percent to about 40 weight percent based on the weight of the total catalyst composition.

The process of this invention can be carried out by means of any apparatus whereby there is achieved an ultimate contact of the catalyst with the organic compound to be reformed and thereafter of the catalyst with the oxygen-containing gas. The process is in no way limited to the use of a particular apparatus. The process of this invention can be carried out using a fixed catalyst bed, fluidized catalyst bed or moving catalyst bed. Because of the attrition resistance of the catalyst and the need for periodic regeneration, the moving catalyst bed is presently preferred in the process of the present invention.

In order to avoid any casual mixing of the organic feed and the oxygen containing fluid utilized in the regeneration step, provision is preferably made for terminating the flow of feed to the reactor and injecting an inert purging fluid such as nitrogen or carbon dioxide. Any purge time suitable to prevent mixing of the organic feed and the oxygen containing fluid can be utilized. The purge duration will generally range from about 1 minute to about 10 minutes and will more preferably range from about 3 minutes to about 6 minutes. Any suitable flow rate of the purge gas may be utilized. Presently preferred is a purge fluid flow rate in the range of about 800 GHSV to about 1200 GHSV.

Any suitable temperature for reforming organic compounds over the zinc titanate hydrogel can be utilized. The reforming temperature will generally be in the range of about 427° to about 593° C. and will more preferably be in the range of about 510° to about 566° C.

Any suitable pressure for the reforming of the organic feedstock over the zinc titanate hydrogel can be utilized. In general, the pressure will be in the range of about 50 to about 700 psig and will more preferably be in the range of about 150 to about 350 psig. The pressure will be in terms of total system pressure where total system pressure is defined as the sum of the partial pressures of the organic feedstock, the hydrogen added to the process, and the hydrogen produced in the process.

Any quantity of hydrogen suitable for substantially preventing the formation of coke can be added to the reforming process. The quantity of hydrogen added will generally be in the range of about 0.5 to about 20 moles per mole of hydrocarbon feed and will more preferably be in the range of about 2 to about 10 moles of hydrogen per mole of feedstock.

Any suitable residence time for the organic feedstock in the presence of the zinc titanate hydrogel can be utilized. In general, the residence time in terms of the volume of liquid feedstock per unit volume of catalyst per hour (LHSV) will be in the range of about 0.1 to about 10 and will more preferably be in the range of about 0.5 to about 5.

Any suitable time for the regeneration of the reforming catalyst can be utilized. The time for the regeneration of the catalyst will generally range from about 5 minutes to about 60 minutes and will more preferably range from about 10 minutes to about 30 minutes. The regeneration effluent should be substantially free of carbon dioxide at the end of the regeneration period.

The amount of oxygen, from any source, supplied during the regeneration step will be at least the amount sufficient to remove substantially all carbonaceous materials from the catalyst. The regeneration step can be conducted at the same temperature and pressure recited for the reforming step although somewhat higher temperatures can be used, if desired.

Catalysis of reforming reactions with the zinc titanate hydrogel is most effective with the use of relatively short process periods with intervening periods of oxidative regeneration. The duration of the reforming process period will generally be in the range of about 1 minute to about 4 hours with a duration of about 5 minutes to about 60 minutes being preferred.

The operating cycle for the reforming process will generally include the successive steps of:
(1) contacting the organic feed with the catalyst to thereby reform the organic feed;
(2) terminating the flow of the organic feed to the reactor;
(3) optionally, purging the catalyst with an inert fluid;
(4) contacting the catalyst with free oxygen to regenerate the catalyst;
(5) terminating the flow of free oxygen to the reactor; and
(6) optionally, purging the thus regenerated catalyst with an inert fluid before repeating step (1).

The following examples are presented in further illustration of the invention.

EXAMPLE 1

Zinc titanate was prepared by mixing Mallinckrodt powdered zinc oxide and of Cab-O-Ti titanium dioxide (flame hydrolyzed) by slurrying in 150 ml of water in a blender for 5 minutes. The ratio of zinc oxide to titanium dioxide used was such as to give an atomic ratio of zinc:titanium in the finished preparation of 1.8:1. The resulting slurry was dried in an oven at 105° C. and then calcined in air for three hours at 816° C. After cooling, the thus calcined material was crushed and screened, and a $-16+40$ mesh fraction was reserved for testing. This preparation is the same as the preparation of the zinc titanate as described in Example 1 of U.S. Pat. No. 4,263,133. A portion of the thus prepared zinc titanate was utilized as the control catalyst.

81.0 grams of the thus prepared powdered zinc titanate was slurried into 500 mL of water and treated with the transducer of an ultrasonic cell disrupter at high power for about 10 minutes to reduce the particle size of the zinc titanate to about 2–10 microns. The resulting slurry was combined with a suspension of 189.1 grams of alpha alumina monohydrate and about 900 mL of water. Sufficient nitric acid was added to the resulting mixture to lower the pH of the resulting mixture from about 7.6 to about 3.0 to produce the hydrosol. 10 mL of concentrated ammonium hydroxide was then added to the hydrosol to produce a hydrogel. The hydrogel was then dried in an oven for 18 hours at 82° C. and then the temperature was increased to 149° C. for 2 more hours. The thru dried hydrogel was then calcined in air in a furnace which was heated to 648° C. during 2 hours and then held at that temperature for 2 hours. The resulting zinc titanate hydrogel contained 35.5 weight percent zinc titanate based on the weight of the total hydrogel. The hydrogel was crushed and screened and a $-16+40$ mesh fraction was reserved for testing.

The zinc titanate catalyst prepared in accordance with the procedure of U.S. Pat. No. 4,263,133 and the zinc titanate hydrogel were used in runs to reform methylcyclopentane. The desired reaction was to isomerize methylcyclopentane to cyclohexane and then dehydrogenate the cyclohexane to benzene. Runs were made using 25 mL of the $-16+40$ mesh catalyst mixed with an equal volume of quartz chips. The catalyst mixed with quartz chips was placed in a stainless steel reactor mounted vertically in a temperature controlled electric furnace. The feed passed downflow through the reactor and the resulting liquid products were collected for subsequent GLC analyses. Analyses of gaseous products ($H_2$ to $C_5$) was based on snap samples taken periodically into a gas chromatograph. All runs were made at 538° C., 300 psig, 1.0 LHSV and a hydrogen:methylcyclopentane feed mole ratio of four. Results of runs with the two catalysts are set forth in Table 1.

TABLE 1

|  | ZINC TITANATE | ZINC TITANATE HYDROGEL |
|---|---|---|
| Time on stream (hrs.) | 1    15 | 106 |
| Methylcyclopentane Conversion (%) | 18.5    13.0 | 78.0/80.9/64.8* |
| Selectivity to Benzene (%) | 32.2    21.8 | 37.8/46.0/41.1* |

*Initial/Maximum/Final

Referring now to Table 1, although the method of reporting results differs, it is apparent that after 15 hours the zinc titanate catalyst has already lost an appreciable fraction of its activity which, at best, was much less than the zinc titanate hydrogel had during a 106 hour run. Regeneration was not used in either of the runs of Table 1.

EXAMPLE 2

Fifty gram portions of a $-80+200$ mesh fraction of the two catalyst of Example 1 were fluidized with air in a cylindrical reactor for 44 hours. Fines smaller than 200 mesh are entrained in the air and caught in a separate vessel for measurement during the test. Results of the attrition test show that the attrition rate (weight loss) is first order and can be characterized by a first order rate constant. When subjected to the attrition test, the rate constant for zinc titanate was about 0.2 hr.$^{-1}$ and for the zinc titanate hydrogel it was about 0.0118 hr.$^{-1}$. For comparison, a commercial fluid cracking catalyst had a rate constant of 0.0066 hr.$^{-1}$ when subjected to the same test.

It can be seen from the attrition test that the zinc titanate hydrogel has a substantially higher attrition resistance than the zinc titanate of U.S. Pat. No. 4,263,133.

Reasonable variations and modifications are possible within the scope of the disclosure and the appended claims to the invention.

That which is claimed is:

1. A catalyst composition comprising a hydrogel of zinc titanate and an acidic carrier.

2. A catalyst composition in accordance with claim 1 wherein the concentration of zinc titanate in said hydrogel is in the range of about 10 to about 50 weight percent based on the weight of the hydrogel.

3. A catalyst composition in accordance with claim 1 wherein the concentration of zinc titanate in said hydrogel is in the range of about 20 to about 40 weight percent based on the weight of the hydrogel.

4. A catalyst composition in accordance with claim 1 wherein said acidic carrier is alumina.

5. A catalyst composition in accordance with claim 1 wherein said zinc titanate is prepared by calcining a mixture of zinc oxide and titanium dioxide in the presence of free oxygen at a temperature in the range of about 650° C. to about 1050° C.

6. A catalyst composition in accordance with claim 5 wherein the atomic ratio of zinc to titanium is in the range of about 1:1 to about 3:1.

7. A catalyst composition in accordance with claim 5 wherein the atomic ratio of zinc to titanium is in the range of about 1.8:1 to about 2.2:1.

8. A catalyst composition in accordance with claim 1 wherein said hydrogel is formed by mixing powdered zinc titanate with a hydrosol of alumina hydrate to form a zinc titanate/alumina hydrosol, adding ammonium hydroxide to convert said hydrosol to a hydrogel and drying and calcining said hydrogel.

9. A catalyst composition in accordance with claim 8 wherein said hydrogel is dried for a time in the range of about 8 to about 24 hours and at a temperature in the range of about 35° C. to about 150° C.

10. A catalyst composition in accordance with claim 9 wherein the dried hydrogel is calcined in the presence of free oxygen at a temperature in the range of about 425° C. to about 650° C. for a time of about 2 hours.

* * * * *